United States Patent
Weinheimer et al.

(10) Patent No.: US 6,299,132 B1
(45) Date of Patent: Oct. 9, 2001

(54) REFLUX VALVE

(75) Inventors: Jacek M. Weinheimer, Treasure Island; Gregory S. Jordan, Palm Harbor, both of FL (US)

(73) Assignee: Halkey-Roberts Corporation, St. Petersburg, FL (US)

( * ) Notice: Subject to any disclaimer, the term of this patent is extended or adjusted under 35 U.S.C. 154(b) by 0 days.

(21) Appl. No.: 09/523,354

(22) Filed: Mar. 10, 2000

Related U.S. Application Data (60) Provisional application No. 60/127,143, filed on Mar. 31, 1999.

(51) Int. Cl.⁷ .................................................. A61M 5/34
(52) U.S. Cl. .................................. 251/149.6; 251/149.1; 604/249
(58) Field of Search ............................. 251/149.6, 149.1; 604/33, 249, 905

(56) References Cited

U.S. PATENT DOCUMENTS

| | | |
|---|---|---|
| 3,538,950 * | 11/1970 | Porteners ................. 251/149.6 X |
| 3,806,086 | 4/1974 | Cloyd ................... 251/149.1 |
| 4,176,681 | 12/1979 | Mackal . |
| 4,305,425 | 12/1981 | Mackal et al. . |
| 4,541,658 * | 9/1985 | Bartholomew ........... 251/149.6 X |
| 4,681,132 | 7/1987 | Lardner . |
| 4,744,391 | 5/1988 | Lardner . |
| 4,776,369 | 10/1988 | Lardner et al. . |
| 4,917,668 | 4/1990 | Haindl . |
| 4,998,562 | 3/1991 | Foltz . |
| 5,080,654 | 1/1992 | Picha et al. . |
| 5,108,380 | 4/1992 | Herlitze et al. . |
| 5,242,393 | 9/1993 | Brimhall et al. . |
| 5,330,435 | 7/1994 | Vaillancourt . |
| 5,349,984 | 9/1994 | Weinheimer et al. . |
| 5,353,837 * | 10/1994 | Faust ..................... 251/149.7 X |
| 5,360,413 | 11/1994 | Leason et al. . |
| 5,380,306 | 1/1995 | Brinon . |
| 5,385,331 * | 1/1995 | Allread et al. ............ 251/149.1 |
| 5,474,536 | 12/1995 | Bonaldo . |
| 5,474,544 | 12/1995 | Lynn . |
| 5,501,426 | 3/1996 | Atkinson et al. . |
| 5,509,433 | 4/1996 | Paradis . |
| 5,509,912 | 4/1996 | Vaillancourt et al. . |
| 5,520,666 | 5/1996 | Choudhury et al. . |
| 5,533,708 | 7/1996 | Atkinson et al. . |
| 5,549,566 | 8/1996 | Elias et al. . |
| 5,582,202 * | 12/1996 | Schultz et al. ............. 251/149.6 X |
| 5,616,130 | 4/1997 | Mayer . |
| 5,697,410 * | 12/1997 | Rutter et al. ............. 251/149.6 X |
| 5,699,821 | 12/1997 | Paradis . |
| 5,796,419 * | 8/1998 | Clark et al. ............. 251/149.6 X |
| 5,806,832 * | 9/1998 | Larbuisson ............... 251/149.6 |
| 5,820,601 | 10/1998 | Mayer . |
| 6,036,171 | 3/2000 | Weinheimer et al. . |

* cited by examiner

Primary Examiner—Kevin Shaver
Assistant Examiner—Eric Keasel
(74) Attorney, Agent, or Firm—Trexler, Bushnell, Giangiorgi, Blackstone & Marr, Ltd.

(57) ABSTRACT

A reflux valve engageable with corresponding structure, such as with another corresponding valve or instrument. The reflux valve includes an actuator which is located in, and shiftable in, a valve body. When the corresponding structure is engaged with the actuator, the actuator shifts in the valve body, and pushes a valve stem out of engagement with a valve seat. As a result, liquid is allowed to flow, in one direction, through the actuator, past the valve seat, along an area adjacent a periphery of the valve stem, and out the valve body. Preferably, when the valve stem is unseated from the valve seat, liquid can also flow in an opposite direction, i.e. along an area adjacent a periphery of the valve stem, past the valve seat, through the actuator, and out the valve body. Preferably, a spring or an extended end portion of the valve stem biases the valve stem into the valve seat. Regardless, preferably the valve stem unseats from the valve seat only upon the actuator being engaged by the corresponding structure. Preferably, the actuator is configured such that guide structure which is typically provided on prior art valves can be eliminated.

16 Claims, 6 Drawing Sheets

REFLUX VALVE

RELATED APPLICATION

This application claims the benefit of U.S. Provisional Application Ser. No. 60/127,143, filed Mar. 31, 1999.

BACKGROUND

The present invention relates generally to valves, and relates more specifically to a novel valve construction that provides many advantageous features, and is well adapted for medical usage, such as in needleless IV sets, and other medical applications where it is desirable to avoid use of needles in the transmission and delivery of fluid products to patients in a sterile environment.

Presently, there are many types of valves, such as check valves, which are designed to control the one-way flow of a fluid therethrough. One common type of check valve comprises a valve element, such as a ball or a spring biased valve stem, reciprocatingly positioned within a valve body providing a fluid passageway. The flow of fluid in one direction through the valve body is permitted upon displacement of the stem as it flows around the valve element to exit the valve body. However, in the opposite direction, the flow of fluid, along with the spring, forces the valve element against a valve seat, thereby inhibiting, or checking, the flow of fluid therethrough. In this manner, this type of check valve effectively provides that fluid can flow only in one direction through the check valve. An example of this type of valve can be found in U.S. Pat. No. 5,349,984.

It is advantageous to provide that IV sets are needleless. By providing that IV sets are needleless, doctors, nurses and other medical technicians who handle the IV sets are less likely to be punctured accidentally by the IV set. As a result of the AIDS epidemic, it is presently very important to reduce the likelihood that any unintended persons become accidentally punctured, such as by IV sets, in a medical environment.

It is also advantageous to provide that components of an IV set can be quickly and easily interconnected so that an IV set can be assembled and disassembled quickly and easily. It is also advantageous to provide that the components of an IV set, such as the valves thereof, are cost-effective to manufacture.

OBJECTS AND SUMMARY OF THE DISCLOSURE

A general object of the present invention is to provide a reflux valve which can be employed in a needleless IV set.

Another object of the present invention is to provide a reflux valve which can be quickly and easily installed, such as in a needleless IV set.

Yet another object of the present invention is to provide a reflux valve which is cost-effective to manufacture.

Still another object of the present invention is to provide a reflux valve which restricts fluid flow therethrough without requiring fluid pressure in the opposite direction.

Yet another object of the present invention is to provide a reflux valve which allows fluid flow in both directions upon a stem being displaced within the valve.

Briefly, and in accordance with the above, the present invention envisions a reflux valve engageable with corresponding structure, such as with another corresponding valve or instrument. The reflux valve includes an actuator which is located in, and shiftable in, a valve body. When the corresponding structure, such as another valve or instrument, is engaged with the actuator, the actuator shifts in the valve body, and pushes a valve stem out of engagement with a valve seat. As a result, liquid is allowed to flow, in one direction, through the actuator, past the valve seat, along an area adjacent a periphery of the valve stem, and out the valve body. Preferably, when the valve stem is unseated from the valve seat, liquid can also flow in an opposite direction, i.e. along an area adjacent a periphery of the valve stem, past the valve seat, through the actuator, and out the valve body. Preferably, a spring or an extended end portion of the valve stem biases the valve stem into the valve seat. Regardless, preferably the valve stem unseats from the valve seat only upon the actuator being engaged by the corresponding structure.

Preferably, the actuator of the reflux valve provides a male component which inserts in a female member, causing structure in the female member to engage the actuator resulting in the actuator unseating the valve stem from the valve seat, thereby allowing fluid to flow in both directions through the reflux valve. Preferably, the valve body of the reflux valve is configured to receive the corresponding structure in a Luer lock arrangement.

BRIEF DESCRIPTION OF THE DRAWINGS

The organization and manner of the structure and function of the invention, together with further objects and advantages thereof, may be understood by reference to the following description taken in connection with the accompanying drawings, wherein like reference numerals identify like elements, and in which.

DESCRIPTION

Figure 8:
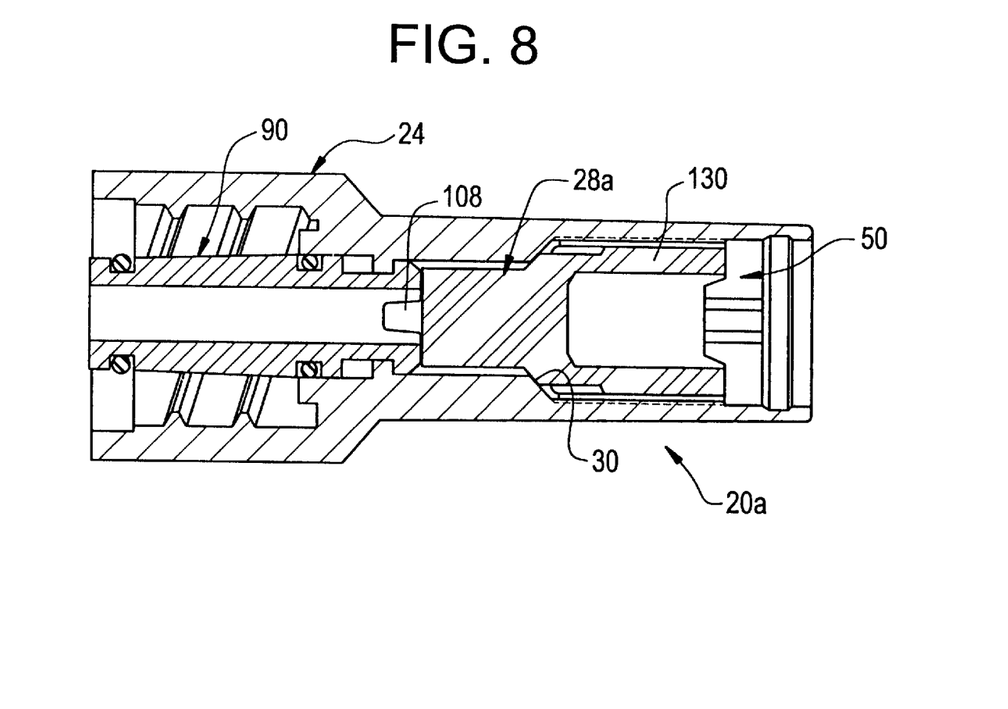
FIG. 8 is an enlarged, cross-sectional view of a reflux valve which is in accordance with another embodiment of the present invention, showing the valve in a closed position.
Figure 9:
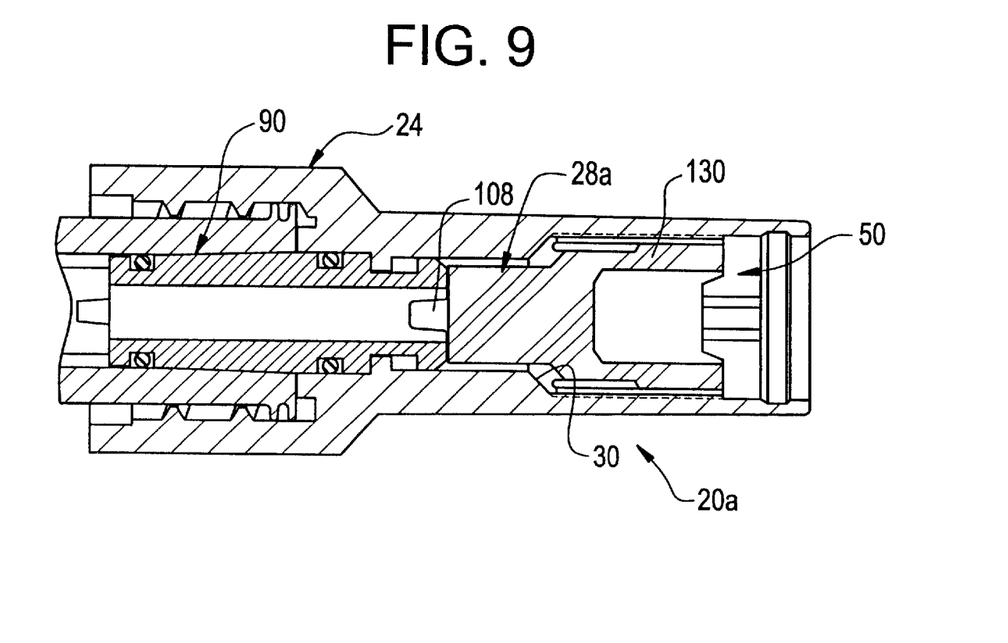
FIG. 9 is an enlarged, cross-sectional view, similar to FIG. 8, of the reflux valve of FIG. 8, showing corresponding structure, such as either one of the valves shown in FIG. 13 or 14, engaged with the reflux valve causing the reflux valve to be in an open position, thereby allowing fluid to flow through the reflux valve.

Shown in the drawings are two reflux valves 20, 20a which are in accordance with embodiments of the present invention. Specifically, FIGS. 1 and 2 illustrate a reflux valve 20 which is in accordance with one embodiment of the present invention, and FIGS. 8 and 9 illustrate a reflux valve 20a which is in accordance with another embodiment of the present invention.

Both reflux valves 20 and 20a are configured to be quickly and easily installed, such as in a needleless IV set, and both reflux valves 20 and 20a are cost-effective to manufacture. Both reflux valves 20 and 20a restrict fluid flow in one direction without requiring fluid pressure in the opposite direction, yet permit fluid flow in either direction upon a valve stem being displaced from a valve seat. Both reflux valves 20 and 20a seal to restrict fluid flow therethrough unless corresponding structure 200, such as a corresponding valve or instrument, is engaged with the valve thereby causing the valve stem to unseat from the valve seat.

The reflux valve 20 illustrated in FIGS. 1 and 2 will now be described. The reflux valve 20 includes a valve body 24 and a valve stem 28 disposed in the valve body 24. When the reflux valve 20 is in a closed position, as shown in FIG. 1, the valve stem 28 is seated or engaged in a valve seat 30 in the valve body 24. In contrast, when the reflux valve 20 is in an open position, as shown in FIG. 2, the valve stem 28 is shifted in the valve body 24, and is unseated or disengaged from the valve seat 30 in the valve body 24. When the reflux valve 20 is in the closed position, as shown in FIG. 1, fluid cannot flow through the valve 20. In contrast, when the reflux valve 20 is in the open position, as shown in FIG. 2, fluid can flow in either direction through the valve 20.

Figure 1:
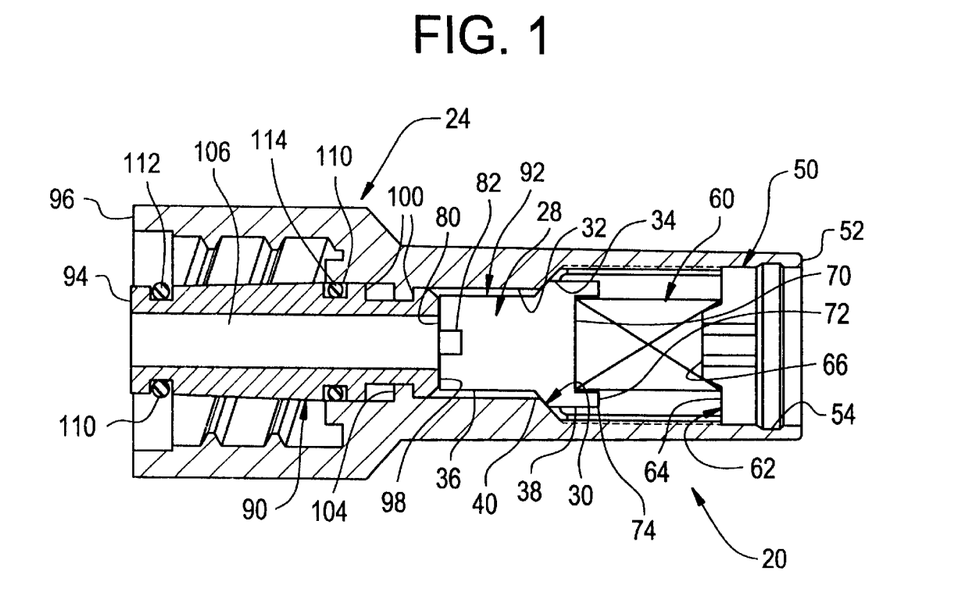
FIG. 1 is an enlarged, cross-sectional view of a reflux valve which is in accordance with an embodiment of the present invention, showing the reflux valve in a closed position.
Figure 2:
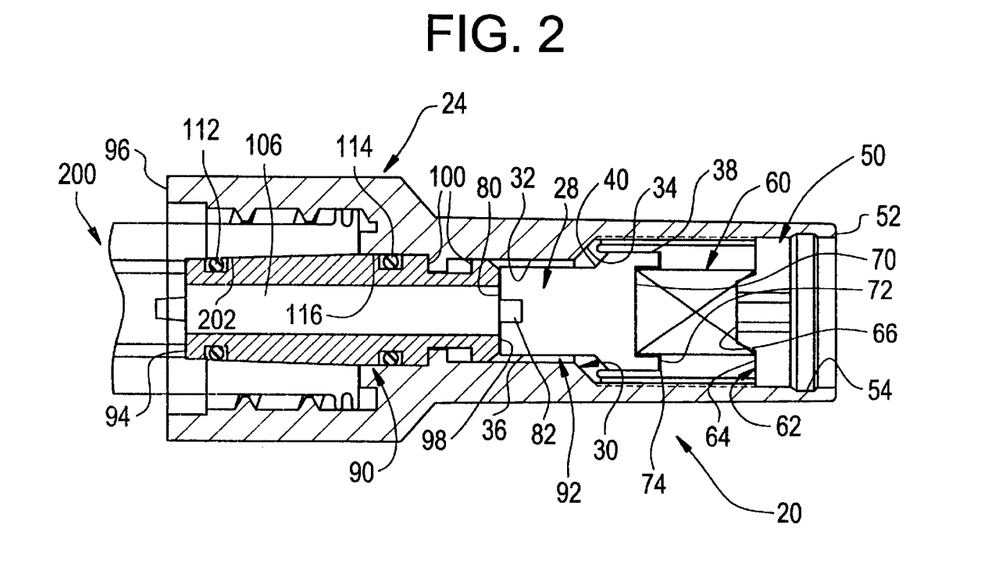
FIG. 2 is an enlarged, cross-sectional view, similar to FIG. 1, of the reflux valve of FIG. 1, showing corresponding structure, such as either one of the valves shown in FIG. 13 or 14, engaged with the reflux valve causing the reflux valve to be in an open position, thereby allowing fluid to flow through the reflux valve.
Figure 4:
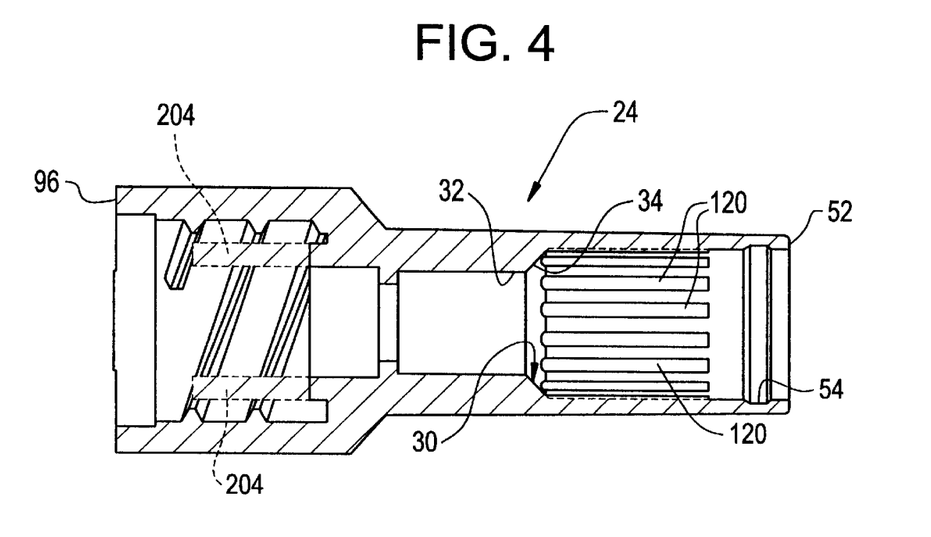
FIG. 4 is cross-sectional view, taken along line 4—4 of FIG. 3, of the valve body illustrated in FIG. 3.

As shown in FIGS. 1, 2 and 4, the valve seat 30 in the valve body 24 is preferably defined by a portion of an internal wall 32 of the valve body 24, where the portion defines an inclined surface 34. As shown in FIGS. 1 and 2, the valve stem 28 may provide two generally cylindrical portions 36 and 38 and a frusto-conical portion 40 disposed between the two generally cylindrical portions 36 and 38. As shown in FIG. 1, the frusto-conical portion 40 of the valve stem 28 contacts the inclined surface 34 of the internal wall 32 of the valve body 24 to provide that the valve 20 is closed. In contrast, as shown in FIG. 2, the frusto-conical portion 40 of the valve stem 28 disengages from the inclined surface 34 of the internal wall 32 of the valve body 24 to provide that the valve 20 is open. The opening and closing of the valve 20 will be discussed more fully later herein.

Figure 3:
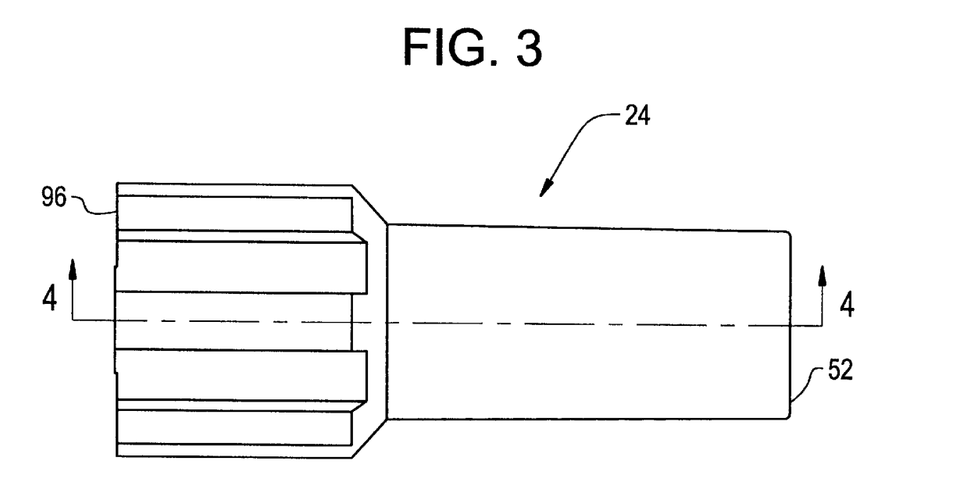
FIG. 3 is an enlarged, side, elevational view of a valve body of the reflux valve shown in FIGS. 1 and 2.
Figure 7:
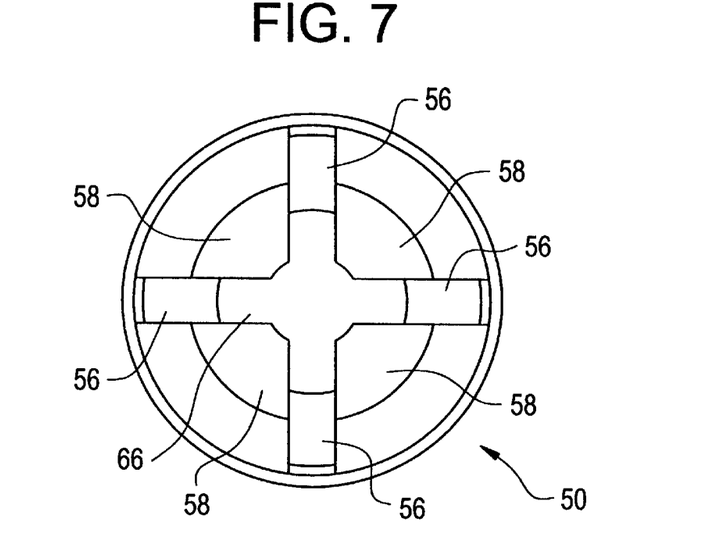
FIG. 7 is an enlarged, front, elevational view of a plug of the reflux valve shown in FIGS. 1 and 2.

As shown in FIGS. 1 and 2, a plug 50 is retained on the valve body 24, generally proximate an end 52 of the valve body 24. The plug 50 is retained in a recess 54 in the internal wall 32 of the valve body 24. The recess 54 in the valve body 24 can also be viewed in FIG. 4, which is a cross-sectional view of the valve body 24 taken along line 4—4 of FIG. 3. As shown in FIG. 7, the plug 50 is generally circular, and provides a plurality of fins 56 providing fluid passageways 58 therebetween. As will be described later herein, fluid which flows through the valve 20 when the valve 20 is in the open position, as shown in FIG. 2, flows between the fins 56 of the plug and through the fluid passageways 58 provided between the fins 56.

As shown in FIGS. 1 and 2, a compression spring 60 (represented by an "X") is disposed between the valve stem 28 and the plug 50. Specifically, a top surface 62 of the plug 50 provides a seat for receiving an end of the compression spring 60, and the seat is provided by an annular surface 64 which generally surrounds a centralized protrusion 66 on the top surface 62 of the plug. The protrusion 66 on the top surface 62 of the plug 50 tends to keep the compression spring 60 generally coaxial with the plug 50 and the valve stem 28. As also shown in FIGS. 1 and 2, a recess 70 is provided on the end 72 of the valve stem 28, and the recess 70 receives the other end of the compression spring 60. Therefore, the recess 70 generally provides a seat for the opposite end of the compression spring 60. An annular protrusion 74 surrounds and essentially defines the recess 70 on the valve stem 28, and the annular protrusion 74 also tends to keep the compression spring 60 generally coaxial with the plug 50 and the valve stem 28.

The opposite end 80 of the valve stem 28 provides a notch 82. In the case where the fluid flow through the reflux valve 20 is from left-to-right in FIG. 2, the notch 82 works to receive fluid from an actuator 90, and deflect the fluid to an area 92 adjacent the periphery of the valve stem 28. In the case where the fluid flow through the reflux valve 20 is from right-to-left in FIG. 2, the notch 82 works to receive fluid from the area 92 adjacent the periphery of the valve stem 28, and direct the fluid to the actuator 90. This will be described more fully later herein.

As shown in FIGS. 1 and 2, the actuator 90 has one end 94 located generally proximate an end 96 of the valve body 24, and has an opposite end 98 which contacts the end 80 of the valve stem 28. As shown in FIGS. 1, 2, 5 and 6, the actuator 90 has shoulders 100 on an outer surface thereof, and, as shown in FIGS. 1 and 2, the shoulders 100 engage an inwardly facing protrusion 104 on the internal surface 32 of the valve body 24. The inwardly facing protrusion 104 in the valve body 24 engages the shoulders 100 on the actuator 90, and essentially provides a stop which limits the range of travel of the actuator 90 within the valve body 24, which travel occurs when corresponding structure 200, such as another valve or an instrument, engages the end 94 of the actuator 90, as will be described more fully later herein.

Figure 6:
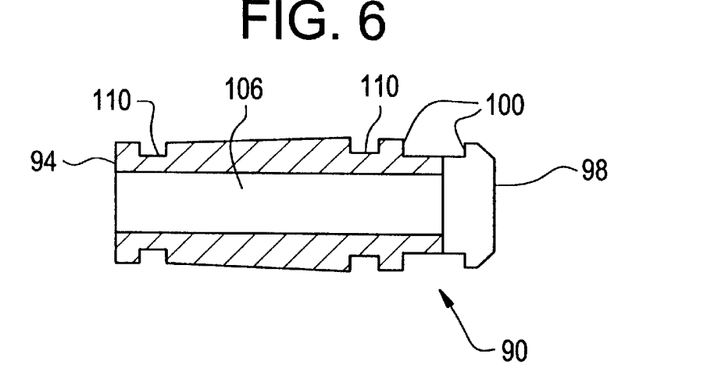
FIG. 6 is cross-sectional view, taken along line 6—6 of FIG. 5, of the actuator illustrated in FIG. 5.

As shown in FIGS. 1, 2 and 6, the actuator 90 has a central bore 106 therein. The central bore 106 essentially provides a fluid passageway through the actuator 90. In the case where the fluid flow through the reflux valve 20 is from left-to-right in FIG. 2, the central bore 106 in the actuator 90 provides a fluid passageway which carries the fluid to the notch 82 in the valve stem 28, and the notch 82 deflects the fluid to the area 92 adjacent the periphery of the valve stem 28. In the case where the fluid flow through the reflux valve 20 is from right-to-left in FIG. 2, the central bore 106 in the actuator 90 provides a fluid passageway which receives fluid from the notch 82 in the valve stem, which fluid has traveled to the notch 82 from the area 92 adjacent the periphery of the valve stem 28.

Figure 5:
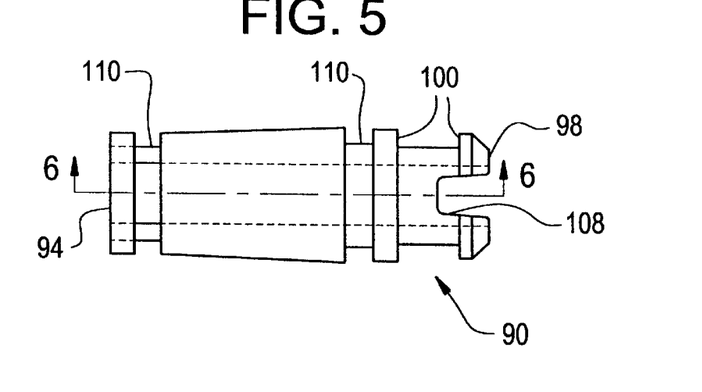
FIG. 5 is an enlarged, side, elevational view of an actuator of the reflux valve shown in FIGS. 1 and 2.

In addition to, or in the alternative to, providing a notch 82 in the valve stem 28, a notch 108 may be provided in the actuator 90, at a position generally proximate the end 98 thereof, as shown in FIG. 5 for allowing fluid to flow into and out of the central bore 106 of the actuator 90, within the valve body 24.

As shown in FIGS. 1, 2, 5 and 6, a pair of recesses 110 are provided on the external surface of the actuator 90 for receiving retaining members 112 and 114, such as rubber or silicone o-rings. As shown in FIG. 2, the one retaining member 114 on the actuator 90 engages an internal wall 116 of the valve body 24 to provide a seal therewith, and the other retaining member 112 on the actuator 90 engages, and provides a seal with, an internal wall 202 of corresponding structure 200 which engages with the end 96 of the valve body 24 to cause the reflux valve 20 to open.

As shown in FIGS. 1, 2, 5 and 6, the external surface of the actuator 90 preferably provides a taper from one end 98 to the other end 94, and the taper may be approximately a 6% taper. The taper generally provides that the actuator 90 is optimally configured for engaging corresponding structure 200 which is engaged with the end 96 of the reflux valve 20 to open the valve. Preferably, the actuator 90 is configured such that guide structure 204 (illustrated in phantom in FIG. 4) which is typically provided on prior art valves can be eliminated.

The corresponding structure 200 which is engaged with the reflux valve 20, and the resulting fluid flow will now be described. The corresponding structure 200 may be another valve or an instrument, or may be essentially any other structure which corresponds to the end 96 of the valve body 24 and the actuator 90 therein. As shown in FIGS. 1, 2 and 4, preferably the end 96 of the valve body 24 is configured to receive the corresponding structure 200 in a Luer lock arrangement. However, this is not imperative to the present invention.

Figure 13:
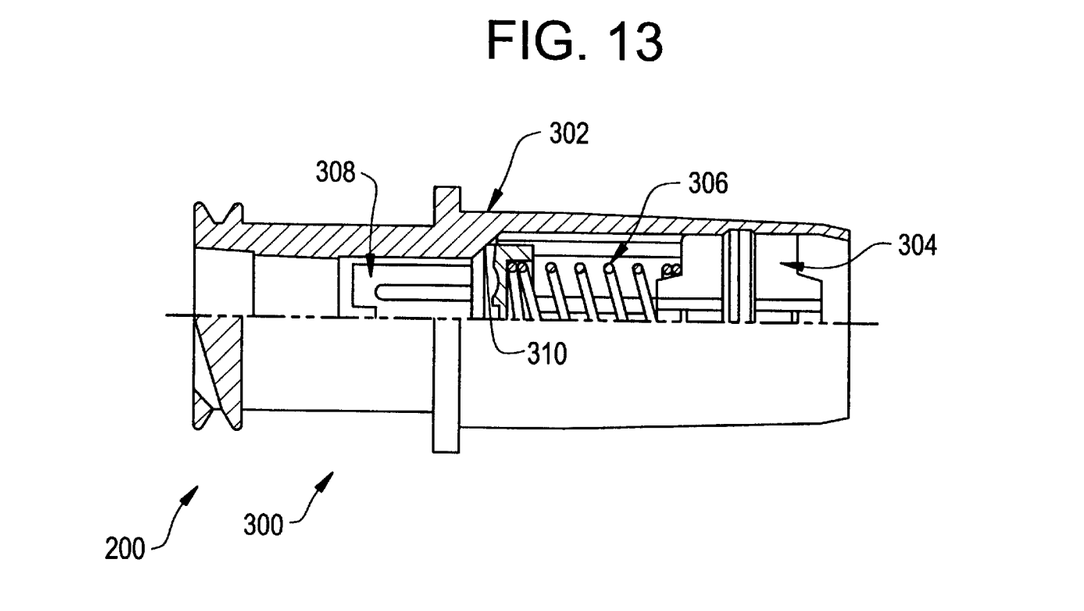
FIG. 13 is an enlarged view, partially in section, of a valve which can be connected to either one of the reflux valves shown in FIG. 1 or 8 in order to place them in the open condition as shown in FIGS. 2 and 9, respectively.
Figure 14:
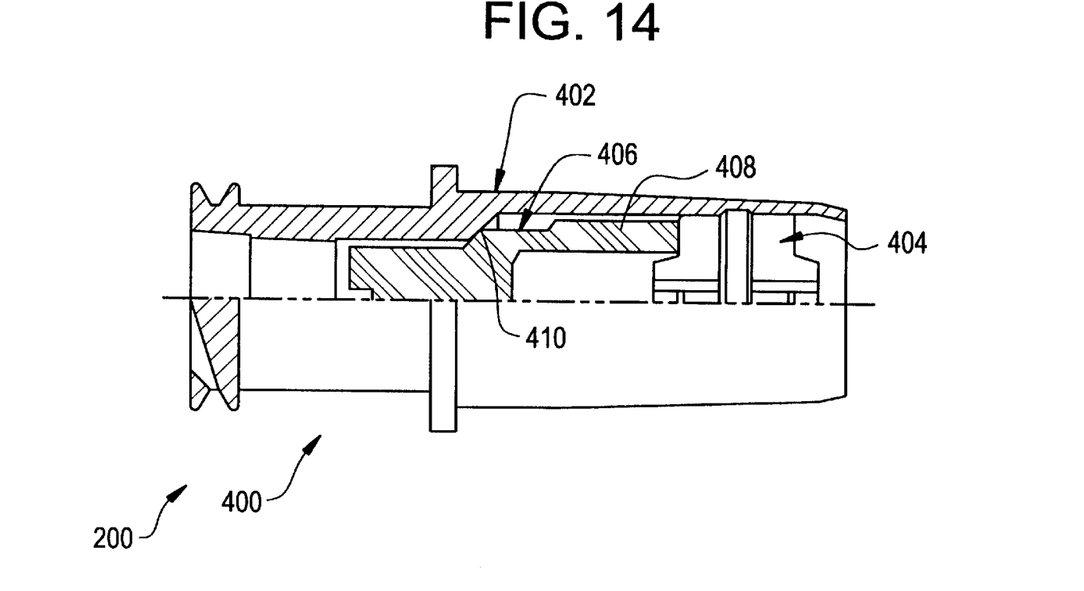
FIG. 14 is an enlarged view, partially in section, of another valve which can be connected to either one of the reflux valves shown in FIG. 1 or 8 in order to place them in the open condition as shown in FIGS. 2 and 9, respectively.

The corresponding structure 200 which is engaged with the end 96 of the reflux valve 20 may consist of another valve such as the valve 300 shown in FIG. 13, or the valve 400 shown in FIG. 14. The valve 300 illustrated in FIG. 13, much like the reflux valve 20 shown in FIGS. 1 and 2, provides a valve body 302 which houses a plug 304, a compression spring 306 and a valve stem 308, where the compression spring 306 biases the valve stem 308 into a valve seat 310. However, the valve 200 does not include an actuator. The valve 400 illustrated in FIG. 14, also provides a valve body 402 which houses a plug 404 and a valve stem 406. However, the valve 400 does not include an actuator or a compression spring. Instead of providing a compression spring, the valve provides that the valve stem 406 has an extended end portion 408 which engages the plug 404 and provides that the valve stem 406 is biased into a valve seat 410.

Because FIG. 2 only depicts the front portion of the corresponding structure 200 which is engaged with the reflux valve 20, and the front portion of the valves 300 and 400 shown in FIGS. 13 and 14, respectively, are identical, the corresponding structure 200 shown in FIG. 2 can relate to either one of the valves 300 and 400 shown in FIGS. 13 and 14. Alternatively, the reflux valve 20 may be configured to engage with corresponding structure which looks essentially completely different than the valves shown in FIGS. 2, 13 and 14.

As the corresponding structure 200 is engaged with the reflux valve 20, and specifically as the corresponding structure 200 is threaded onto the end 96 of the valve body 24 of the reflux valve 20, the front-most retaining member 112 on the actuator 90 engages the internal wall 202 of the corresponding structure 200 causing the actuator 90 to shift in the valve body 24 as the corresponding structure is further driven into the end 96 of the valve body 24. Once the corresponding structure 200 is fully engaged with the end 96 of the valve body 24, the actuator 90 presses the valve stem 28 out of engagement with the valve seat 30 causing the compression spring 60 to compress between the valve stem 28 and the plug 50. At that time, the reflux valve 20 is in the open position, as shown in FIG. 2. In this position, fluid can flow in either direction through the reflux valve 20. In other words, fluid can flow from the corresponding structure 200 to the reflux valve 20 and out the plug 50 at the end 52 of the reflux valve 20, or fluid can flow in the plug 50 at the end 52 of the reflux valve 20, through the reflux valve 20 and to the corresponding structure 200. The fluid flow within the reflux valve 20 itself will now be described in detail.

When the reflux valve 20 is in the open position, as shown in FIG. 2, the valve stem 28 is disengaged from the valve seat 30. This provides that fluid can ultimately flow from the bore 106 provided in the actuator 90 to an area 92 adjacent the periphery of the valve stem 28, or vice versa if the fluid is flowing in the opposite direction. In the case where the fluid flows from left-to-right in FIG. 2, fluid initially enters the bore 106 in the actuator 90, and travels to the notch 82 in the valve stem 28. The notch 82 deflects the fluid to the area 92 adjacent the periphery of the valve stem 28, and the fluid flows along the external surface of the valve stem 28, past the valve seat 30, along the compression spring 60, and out the plug 50, and specifically between the fins 56 of the plug 50 and out the reflux valve 20. In the opposite direction, fluid flows in the plug 50 of the reflex valve 20, along the compression spring 60, past the valve seat 30, along the periphery of the valve stem 28, to the notch 82 in the valve stem 28, to the bore 106 in the actuator 90 and out the end 94 of the actuator 90. As mentioned above, a notch 108 can be provided proximate the end 98 of the actuator 90 (see FIG. 5), either in addition to or instead of providing a notch 82 in the valve stem 28. If a notch 108 is provided in the actuator 90, the notch 108 in the actuator 90, like the notch 82 in the valve stem 28, provides that fluid can flow between the bore 106 in the actuator 90 and the area 92 adjacent the periphery of the valve stem 28. As shown in FIG. 4, to facilitate fluid flow proximate the end 52 of the reflux valve 20, in the area where the valve stem 28 and compression spring 60 are generally located (see FIGS. 1 and 2), longitudinal recesses 120 may be provided in the valve body 24.

The reflux valve 20a illustrated in FIGS. 8 and 9 is very much like the reflux valve 20 shown in FIGS. 1 and 2. Therefore, identical reference numerals are used to identify identical parts, and a detailed description thereof is omitted. Additionally, with regard to parts which are not identical, but do find a corresponding part in the reflux valve 20 already described, the identical reference numeral is used, and the alphabetic suffix "a" is added. With regard to these parts, generally only the differences will be discussed.

The basic difference between the reflux valve 20a shown in FIGS. 8 and 9 and the reflux valve 20 shown in FIG. 1 and 2, which has been described in detail above, is that, unlike the reflux valve 20 shown in FIGS. 1 and 2, the reflux valve 20a shown in FIGS. 8 and 9 does not include a compression spring inside the valve body 24. Instead, the reflux valve 20a provides that the valve stem 28a thereof includes an extended end portion 130 which engages the plug 50 and provides that the valve stem 28a is biased into the valve seat 30. Engagement of the corresponding structure 200 with the actuator 90 causes the actuator 90 to press the valve stem 28a out of engagement with the valve seat 30 and causes the extended end portion 130 of the valve stem 28a to compress and deform in the valve body 24.

Additionally, the valve stem 28a does not include a notch for carrying fluid between the actuator 90 and the area adjacent the periphery of the valve stem 28a. Instead, the design relies solely on the notch 108 in the actuator 90 for this purpose.

Figure 10:
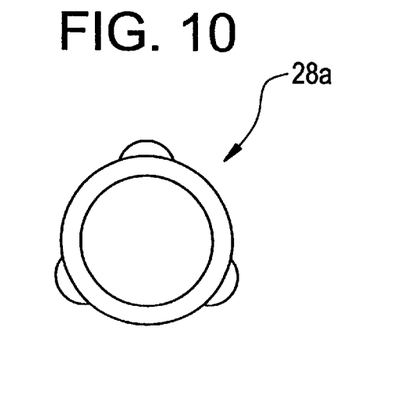
FIG. 10 is an enlarged, front, elevational view of a valve stem of the reflux valve shown in FIGS. 8 and 9.
Figure 11:
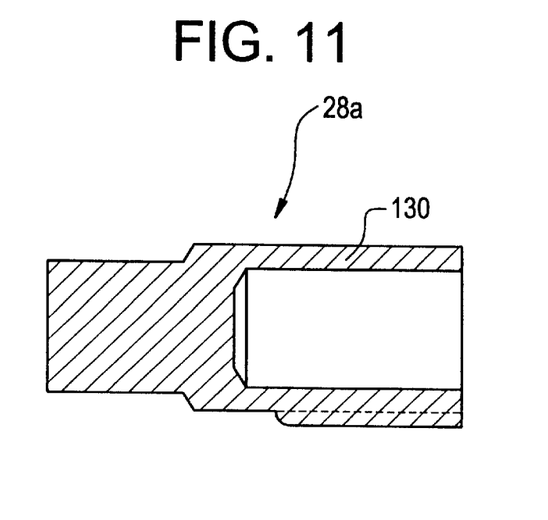
FIG. 11 is an enlarged, side, elevational view of the valve stem shown in FIG. 10.
Figure 12:
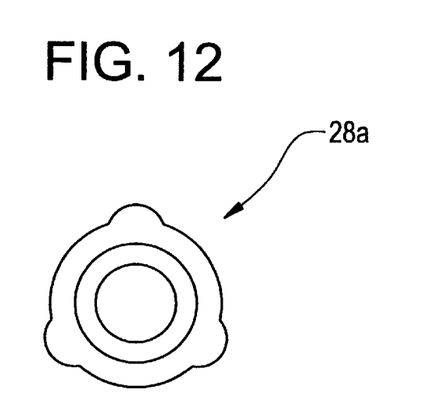
FIG. 12 is an enlarged, rear, elevational view of the valve stem shown in FIGS. 10 and 11.

The valve stem 28a of the reflux valve 20a shown in FIGS. 8 and 9 is shown in isolation in FIGS. 10, 11 and 12. Fluid flow through the reflux valve 20a when the reflux valve 20a is in the open position, as shown in FIG. 9, is very much the same as the fluid flow though the reflux valve 20 shown in FIG. 2 and already described. Therefore, a detailed description of the fluid flow through the reflux valve is omitted.

With regard to materials of the individual components of the reflux valves 20, 20a shown in FIGS. 1, 2, 8 and 9, preferably the valve body 24, 24a is comprised of polyvinyl chloride (PVC), the actuator 90 is comprised of PVC or polypropylene, the plug 50 is comprised of polypropylene, the valve stem 28, 28a is comprised of silicone, and the compression spring 60 is comprised of metal, such as aluminum.

Both reflux valves 20 and 20a are preferably configured for Luer lock engagement. Hence, both can be quickly and easily installed, such as in a needleless IV set. Additionally, both reflux valves 20 and 20a are relatively cost-effective to manufacture. Because of the bias provided by the compression spring (in the case of the reflux valve 20 shown in FIGS. 1 and 2), or by the extended end portion 130 of the valve stem 28a (in the case of the reflux valve 20a shown in FIGS. 8 and 9), both reflux valves 20 and 20a restrict fluid flow in one direction without requiring fluid pressure in the opposite direction. Both reflux valves 20 and 20a permit fluid flow in either direction upon the valve stem 28, 28a being displaced from the valve seat 30. Both reflux valves 20 and 20a seal to restrict fluid flow therethrough unless corresponding structure 200, such as a corresponding valve or instrument, such as is shown in FIGS. 13 and 14, is engaged with the valve 20, 20a thereby causing the valve stem 28, 28a to unseat from the valve seat 30.

While embodiments of the present invention are shown and described, it is envisioned that those skilled in the art may devise various modifications of the present invention without departing from the spirit and scope of the foregoing disclosure.

What is claimed is:

1. A reflux valve engageable with corresponding structure, said reflux valve comprising: a valve body; an actuator at least partially disposed in said valve body; a valve stem in said valve body, said valve stem biased into a valve seat in said valve body, said actuator shiftable relative to said valve body upon the corresponding structure being engaged with said actuator, wherein said actuator pushes said valve stem out of engagement with said valve seat in said valve body, whereafter liquid is flowable, in one direction, through the actuator, past said valve seat, along an area adjacent a periphery of the valve stem, and out said valve body, and in an opposite direction, along said area adjacent said periphery of said valve stem, past said valve seat, through said actuator, and out said valve body; a first retainer disposed on said actuator and configured to engage the corresponding structure upon the corresponding structure being engaged with said actuator; and a second retainer disposed on said actuator and engaged with an internal wall of said valve body, said valve stem including an integral frusto-conical portion which engages said valve seat to prevent liquid from flowing therepast, said actuator including a notch proximate said valve stem, said notch configured to facilitate the flowing of liquid between said actuator and said valve stem.

2. A reflux valve as recited in claim 1, wherein said valve body is configured to receive the corresponding structure in a Luer lock arrangement.

3. A reflux valve as recited in claim 1, wherein said actuator is keyed to said valve body such that a range of travel of said actuator relative to said valve body is limited.

4. A reflux valve as recited in claim 1, wherein said actuator includes a bore which provides a fluid passageway.

5. A reflux valve as recited in claim 1, wherein said actuator is tapered.

6. A reflux valve as recited in claim 1, wherein said valve body has an internal surface which provides a plurality of longitudinal recesses.

7. A reflux valve as recited in claim 1, further comprising a plug engaged with said valve body, said valve stem including an extended end portion which is engaged with said plug, wherein said extended end portion biases said valve stem generally toward said valve seat.

8. A reflux valve as recited in claim 7, said plug including a protrusion, said protrusion engaging said extended end portion of said valve stem and tending to keep said valve stem generally coaxial with said plug.

9. A reflux valve as recited in claim 7, wherein said plug includes a plurality of alternating fins and fluid passageways.

10. A reflux valve as recited in claim 7, wherein said plug is engaged with said valve body generally at an end of said valve body.

11. A reflux valve as recited in claim 1, further comprising a plug engaged with said valve body, and a spring engaged with said plug and said valve stem, said spring biasing said valve stem generally toward said valve seat.

12. A reflux valve as recited in claim 11, said valve stem including an annular protrusion, said annular protrusion defining a recess which receives said spring, said annular protrusion tending to keep said spring generally coaxial with said valve stem.

13. A reflux valve as recited in claim 11, wherein said plug includes a plurality of alternating fins and fluid passageways.

14. A reflux valve as recited in claim 11, wherein said plug is engaged with said valve body generally at an end of said valve body.

15. A reflux valve as recited in claim 11, said plug including a protrusion, said protrusion engaing said spring and tending to keep said spring generally coaxial with said plug.

16. A reflux valve as recited in claim 15, said valve stem including an annular protrusion, said annular protrusion defining a recess which receives said spring, said annular protrusion tending to keep said spring generally coaxial with said valve stem.

* * * * *

UNITED STATES PATENT AND TRADEMARK OFFICE
CERTIFICATE OF CORRECTION

PATENT NO.     : 6,299,132 B1  
DATED          : October 9, 2001  
INVENTOR(S)    : Jacek M. Weinheimer and Gregory S. Jordan Page 1 of 1

It is certified that error appears in the above-identified patent and that said Letters Patent is hereby corrected as shown below:

<u>Column 8,</u>  
Line 50, "engaing" should read -- engaging --

Signed and Sealed this

Seventh Day of May, 2002

*Attest:*

JAMES E. ROGAN  
*Director of the United States Patent and Trademark Office*

*Attesting Officer*